(12) United States Patent
Starr

(10) Patent No.: US 6,599,252 B2
(45) Date of Patent: Jul. 29, 2003

(54) METHOD AND APPARATUS FOR ANATOMICAL DEADSPACE MEASUREMENT

(75) Inventor: Eric W. Starr, Allison Park, PA (US)

(73) Assignee: Respironics, Inc., Murrysville, PA (US)

( * ) Notice: Subject to any disclaimer, the term of this patent is extended or adjusted under 35 U.S.C. 154(b) by 73 days.

(21) Appl. No.: 09/864,806

(22) Filed: May 24, 2001

(65) Prior Publication Data

US 2001/0049478 A1 Dec. 6, 2001

Related U.S. Application Data

(60) Provisional application No. 60/209,284, filed on Jun. 2, 2000.

(51) Int. Cl.$^7$ .................................................. A61B 5/08
(52) U.S. Cl. ....................................... 600/532; 600/538
(58) Field of Search ................................ 600/529, 531, 600/532, 533, 538

(56) References Cited

U.S. PATENT DOCUMENTS 5,632,281 A    5/1997  Rayburn
6,099,491 A    8/2000  Daniels et al.
6,179,784 B1 *  1/2001  Daniels et al. ............... 600/529
6,217,524 B1   4/2001  Orr et al.
6,254,546 B1   6/2001  Vierto-Oja
6,402,697 B1 *  6/2002  Calkins et al. ............... 600/529

OTHER PUBLICATIONS

Marini et al., "Physiological Basis of Ventialtory Support," Lung Biology in Health and Disease, vol. 118, 1998, pp. 718–727.

* cited by examiner

*Primary Examiner*—Max Hindenburg
*Assistant Examiner*—Navin Natnithithadha
(74) *Attorney, Agent, or Firm*—Michael W. Haas

(57) ABSTRACT

An apparatus and method for determining an anatomical deadspace volume $VD_{ANA}$ of a patient. The apparatus includes a sensor that measures a parameter indicative of the volume of gas exhaled by the patient and a gas analyzer that measures a concentration of a gas constituent in the patient's expiratory flow. A controller determines the patient's anatomical deadspace volume based on signals provided by the sensor and the gas analyzer.

28 Claims, 4 Drawing Sheets

$$V_{INH} = V_{EXH} = V_A + V_{D_{ANA}} + V_D = V_A / V_{D_{ANA}} + V_{D_{ALV}} + V_{D_{REL}}$$

(•) OXYGEN
(○) CARBON DIOXIDE

METHOD AND APPARATUS FOR ANATOMICAL DEADSPACE MEASUREMENT

CROSS-REFERENCE TO RELATED APPLICATIONS

The present invention claims priority under 35 U.S.C. §119(e) from U.S. provisional patent application No. 60/209,284 filed Jun. 2, 2000.

BACKGROUND OF THE INVENTION

1. Field of the Invention

The present invention relates to and apparatus and method for measuring a patient's airway or anatomical deadspace volume non-invasively based on a quantitative measurement of the flow of gas from the patient and a measurement of a constituent of that gas.

2. Description of the Related Art

Medical ventilators are utilized to ventilate a patient by engendering the exchange of gas in the lungs of the patient. It is a goal of medical ventilation, for example, to reduce as much as possible the patient's physiological deadspace $VD_{PHY}$, which is the total amount of volume in the patient where no exchange of oxygen and carbon dioxide occurs. The patient's physiological deadspace volume $VD_{PHY}$ includes (1) the anatomical deadspace volume $VD_{ANA}$, which is the volume of the patient's conducting airway, e.g., the airway from the nose and/or mouth and the alveoli in the lungs, (2) the alveolar deadspace volume $VD_{ALV}$, which is the volume of the lungs where, even during normal unassisted breathing, no exchange of oxygen and carbon dioxide occurs and (3) the relative deadspace volume $VD_{REL}$, which is the volume of the lungs were some exchange of oxygen and carbon dioxide takes place, but the amount of exchange is below that of a normal lung.

An experienced caregiver can estimate to a medically reasonable degree of accuracy a patient's total lung volume or tidal volume $V_T$, which includes the alveolar volume $V_A$, where carbon dioxide and oxygen are exchanged, and the alveolar deadspace volume $VD_{ALV}$ and relative deadspace volume $VD_{REL}$. In contrast to the estimate of the patient's total lung volume, however, an estimate of the patient's anatomical deadspace volume $VD_{ANA}$ is not as accurate. Knowing the patient's anatomical deadspace volume is important because an underestimation of the patient's anatomical deadspace volume can result in the ventilator supplying an insufficient volume of breathing gas to fill the total lung volume of the patient during inhalation. Conversely, an overestimation of the anatomical deadspace volume can result in the ventilator attempting to overfill the patient's lungs, with corresponding patient discomfort and increased risk of pulmonary trauma.

SUMMARY OF THE INVENTION

Accordingly, it is an object of the present invention to provide an apparatus for measuring a patient's anatomical deadspace volume $VD_{ANA}$ that overcomes the shortcomings of conventional measurement/estimation techniques. More specifically, it is an object of the present invention to provide an apparatus that accurately, non-invasively, and repeatedly determines the anatomical deadspace volume of a patient.

This object is achieved according to one embodiment of the present invention by providing an anatomical deadspace measurement apparatus that includes a sensor adapted to measure a parameter indicative of a volume of gas exhaled by a patient during at least an exhalation phase of a respiratory cycle. The apparatus also includes a gas analyzer, such as a capnometer or oxygen analyzer, that measures a concentration of a gas constituent, such as carbon dioxide ($CO_2$) or oxygen ($O_2$), in the patient's expiratory flow. The apparatus further includes a controller that receives the outputs of the sensor and gas analyzer and determines the patient's anatomical deadspace volume based on these outputs. In an exemplary embodiment of the present invention, the controller determines the anatomical deadspace volume of a patient by determining a time $t_1$ that corresponds to a point at which the patient commences exhaling and a time $t_2$ that corresponds to an inflection point in a waveform corresponding to the concentration of the gas constituent measured by the gas analyzer. The controller calculates the volume of gas exhaled by the patient from time $t_1$ to time $t_2$ as the anatomical deadspace volume of the patient.

It is yet another object of the present invention to provide a method of determining an anatomical deadspace volume $VD_{ANA}$ of a patient that does not suffer from the disadvantages associated with conventional measurement/estimation techniques. This object is achieved by providing a method that includes: (1) detecting a parameter indicative of a volume of gas exhaled by a patient, (2) detecting a concentration of a gas constituent in the patient's expiratory gas flow, and (3) determining the patient's anatomical deadspace volume $VD_{ANA}$ based on the detected volumetric flow of gas and the detected concentration of a gas constituent. In an exemplary embodiment of the present invention, the last step, i.e., step (3), includes determining a time $t_1$ that corresponds to a point at which the patient commences exhaling, determining a time $t_2$ that corresponds to an inflection point in a waveform corresponding to the concentration of the gas constituent measured in step (2), and calculating a volume of gas exhaled by the patient from time $t_1$ to time $t_2$ as the anatomical deadspace volume of the patient.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
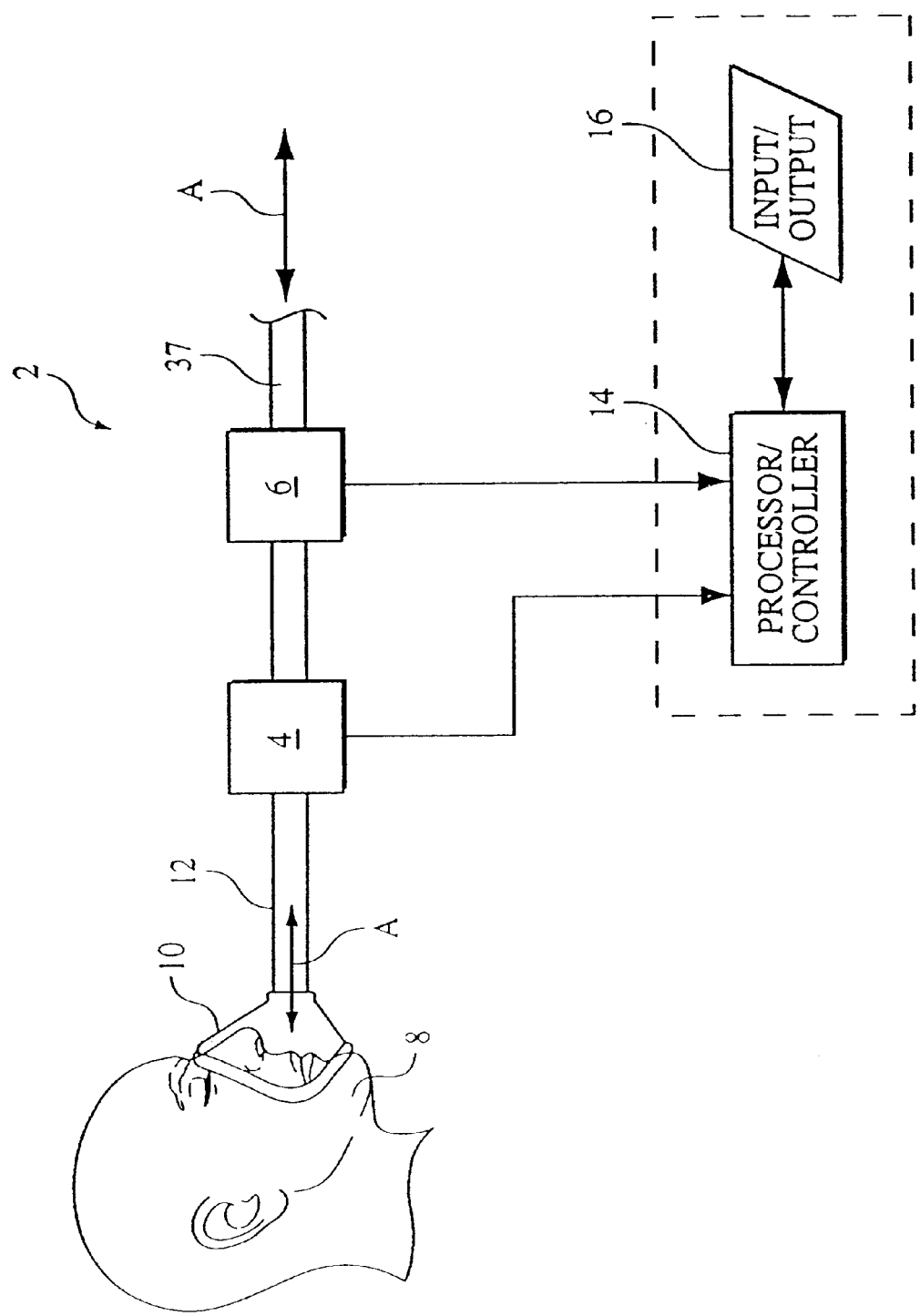
FIG. 1 is a schematic diagram of an apparatus for measuring the anatomical deadspace volume of a patient according to the principles of the present invention.

FIG. 1 schematically illustrates an exemplary embodiment of an anatomical deadspace volume measurement apparatus 2 according to the principles of the present invention. Measurement apparatus 2 includes a sensor 4 and a gas analyzer 6 that are coupled in fluid communication with the airway of a patient 8 via an a patient interface device 10. In the illustrated embodiment, a conduit 12 couples the sensor and gas analyzer to interface 10 so that gas passes through these measurement elements at least during the expiratory phase of the patient's breathing cycle. The patient's inspiratory and expiratory flow are indicated by arrows A in FIG. 1. Patient interface device 10 is any device suitable for communicating a flow of gas between the patient and the sensing elements, such as a nasal mask, full-face mask, tracheal tube, endotracheal tube, nasal pillow, or hood.

In a presently preferred embodiment of the present invention, sensor 4 is a flow sensor that quantitatively measures the rate of flow of gas to and from the patient and provides an output signal indicative thereof to a processor/controller 14. Once the rate of flow of gas from the patient over the expiratory phase of the breathing cycle is known, the volume of gas exhaled by the patient can be determined. In an exemplary embodiment of the present invention, the signal produced by sensor 4 changes magnitude and sign (±) in response to changes in the volumetric gas flow and a direction of flow in conduit 12, respectively. The present invention contemplates that sensor 4 can be any conventional pneumatach flow meter. Another flow meter suitable for use in the anatomical deadspace volume measurement apparatus of the present invention is described in U.S. Pat. No. 6,017,315 to STARR et al., the contents of which are incorporated herein by reference.

Gas analyzer 6 detects a concentration of a constituent of gas in conduit 12 and provides a signal indicative thereof to processor/controller 14. The present invention contemplates that gas analyzer 6 is a conventional capnometer or oxygen analyzer suitable for measuring the concentration of $CO_2$ or $O_2$ in the patient's expiratory flow, respectively. Processor/controller 14 utilizes the output of sensor 4 and gas analyzer 6 to determine the patient's anatomical deadspace in a manner to be described hereinafter. An input/output device 16 is coupled to processor/controller 14 for displaying the output of processor/controller 14.

Figure 2:
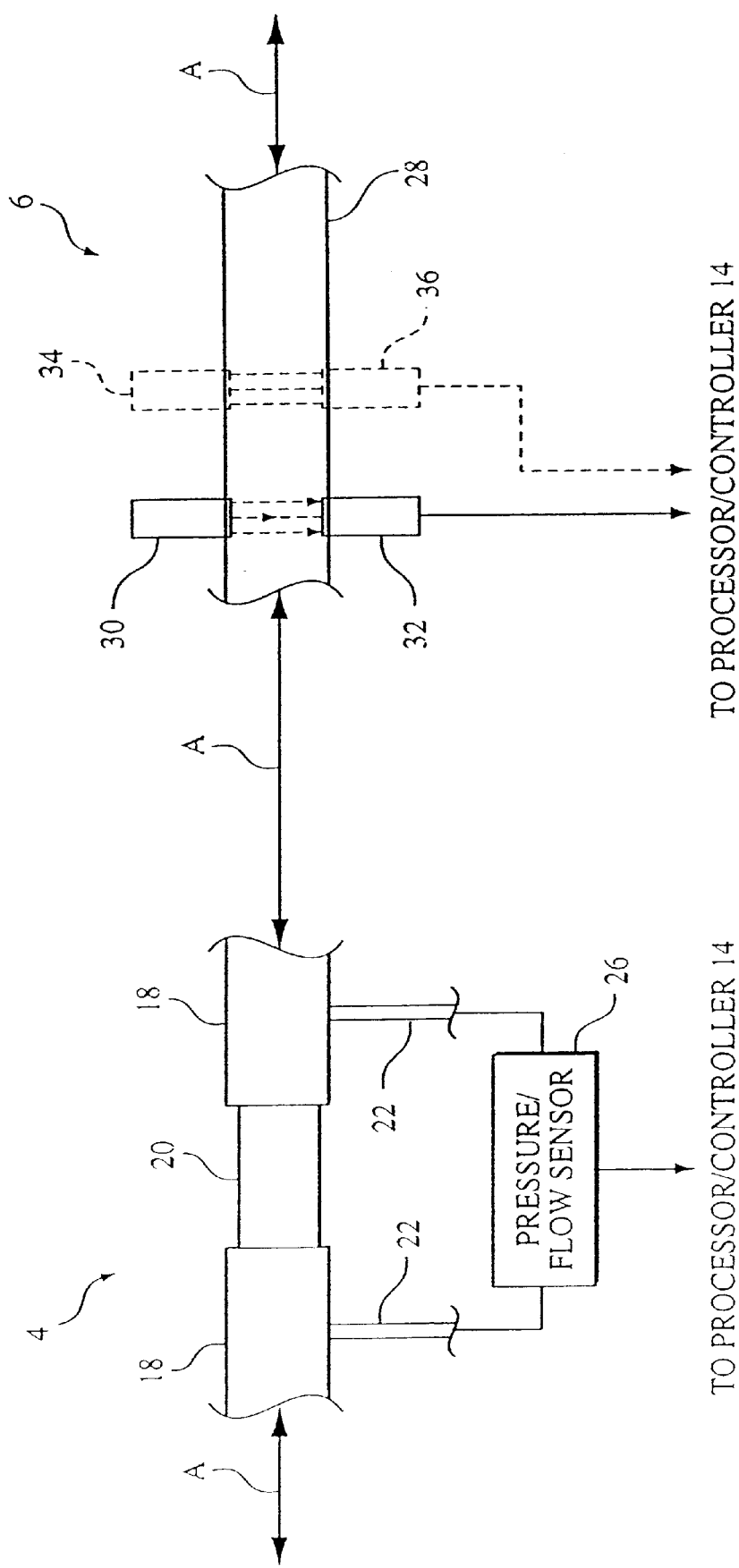
FIG. 2 is a detailed schematic diagram of a flow sensor and a gas analyzer in the apparatus of FIG. 1.

With reference to FIG. 2, and with continuing reference to FIG. 1, an exemplary embodiment of sensor 4 includes a conduit 18 connected in fluid communication with conduit 12. Conduit 18 includes a flow restriction 20, which restricts the flow of gas through conduit 18. A pair of capillary tubes 22 are connected in fluid communication with conduit 18 on opposite sides of flow restriction 20. Capillary tubes 22 are connected to a pressure/flow sensor 26. In one embodiment of the present invention, pressure/flow sensor 26 detects, through capillary tubes 22, a pressure difference in conduit 18 across flow restriction 20. In this embodiment, pressure/flow sensor 26 produces, from the pressure difference, a signal indicative of the volumetric flow of gas in conduit 18. In another embodiment of the present invention, pressure/flow sensor 26 is a mass flow sensor that detects a secondary flow of gas through sensor 26 resulting from flow restriction 20. In this embodiment, pressure/flow sensor 26 also produces a signal indicative of the volumetric flow of gas in conduit 18 based on the measured secondary flow through pressure/flow sensor 26.

In an exemplary embodiment of the present invention, gas analyzer 6 includes a conduit 28 having an IR light source 30 and an IR light detector 32 positioned on opposite sides thereof to detect a concentration of a constituent of gas in conduit 28. IR light source 30 and IR light detector 32 are configured to transmit and receive, respectively, light at a frequency that is selectively blocked by the constituent, e.g., carbon dioxide, to be detected. Gas analyzer 6 can also include, as shown in phantom in FIG. 2, another IR light source 34 and another IR light detector 36 that transmit and receive, respectively, light at a frequency that is selectively blocked by another constituent, e.g., oxygen, to be detected. In response to receiving light from IR light source 30, IR light detector 32 produces a signal indicative of the concentration of the constituent detected thereby. Similarly, if provided, in response to receiving light from IR light source 34, IR light detector 36 produces a signal indicative of the concentration of the constituent detected thereby. It can be appreciated that the present invention contemplates that gas analyzer can detect the concentration of the carbon dioxide, oxygen or both during at least the expiratory phase of the patient's breathing cycle.

It is to be understood that sensor 4 and gas analyzer 6 need not be connected to the patient interface device in the order shown in FIG. 1. Furthermore, other flow sensing and gas analyzing devices can be provided to ensure the accuracy of the flow and gas constituent measurements. The present invention contemplates that an outlet 37 of the flow sensor and gas analyzer assembly is in fluid communication with a gas source, such as ambient atmosphere, a ventilator, or other pressure support device.

Figure 3:
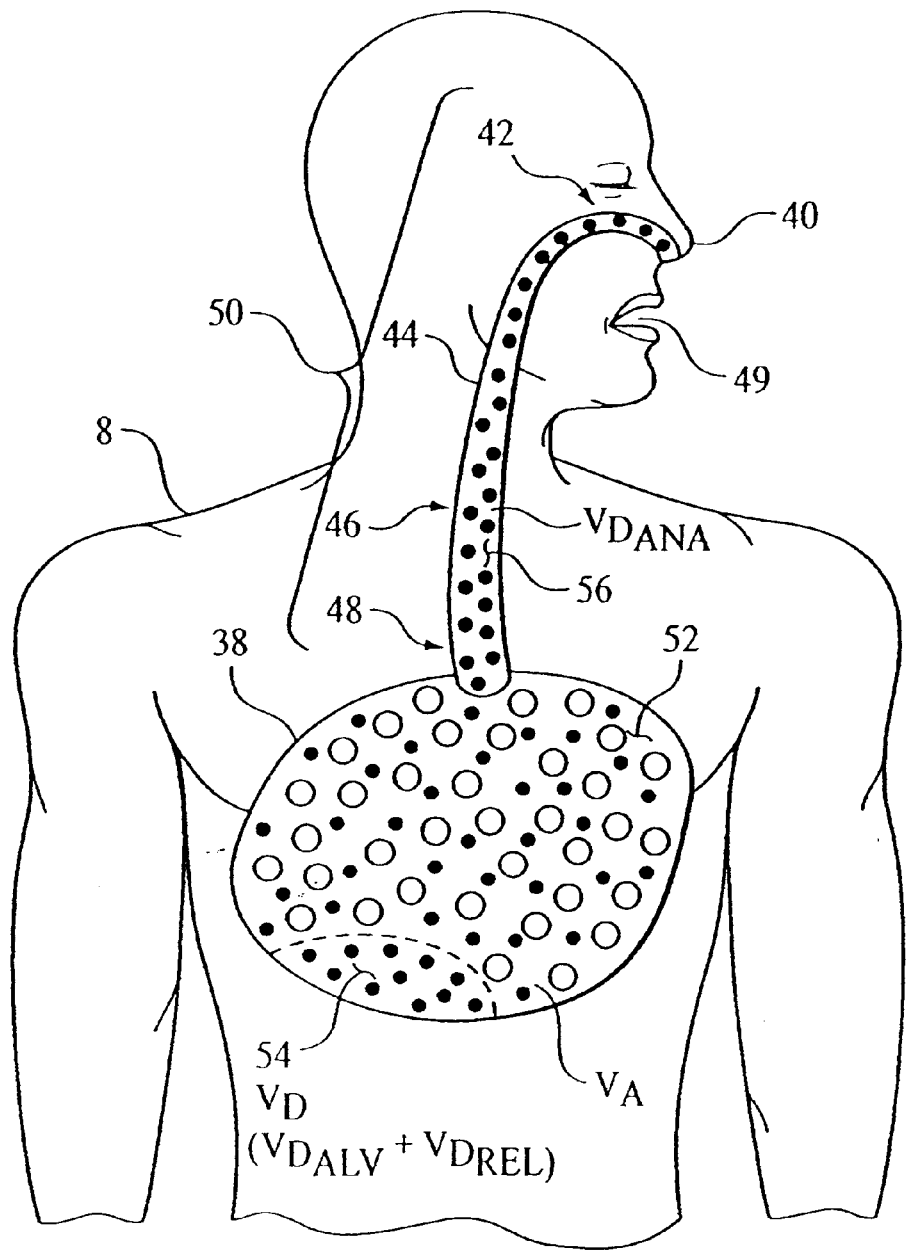
FIG. 3 is a schematic diagram of a human pulmonary system.

FIG. 3 is a schematic diagram of a human pulmonary system helpful in understanding the anatomical deadspace volume measurement apparatus and method of the present invention. Breathing gas entering lungs 38 via nose 40 passes sequentially through a nasal cavity 42, larynx 44, trachea 46 and bronchus 48, hereinafter collectively referred to as airway 50. Of course, gas entering the patient via mouth 49 follows a similar path except that it first passes through the oral cavity. Gas from bronchus 42 is received in alveoli (not shown) of lungs 38 via bronchioles (not shown). The alveoli exchange oxygen in the breathing gas inhaled by patient 8 for carbon dioxide received from blood flowing in pulmonary capillaries surrounding the alveoli. During exhalation, carbon dioxide-filled gas is exhaled from lungs 38 through nose 42 via airway 50.

The total volume of lungs 38 consists of the alveolar volume $V_A$ 52, and a deadspace volume $V_D$ 54. Deadspace volume $V_D$ 54 includes the alveolar deadspace $VD_{ALV}$, in which no exchange of carbon dioxide and oxygen occur and the relative deadspace volume $VD_{REL}$ in which relatively little exchange of carbon dioxide and oxygen occurs. It is to be appreciated that the transition between $V_A$ 52 and $V_D$ 54 in lungs 38 is gradual and therefore, the values of $V_A$ 52 and $V_D$ 54 for each patient are approximations. When patient 8 inhales, a volume of oxygen-rich gas ($V_{INH}$) fills the total volume of lungs 38, i.e., $V_A$ 52 and $V_D$ 54, and also fills the patient's airway 50, which has an anatomical deadspace volume $VD_{ANA}$ 56.

In lungs 38, oxygen, shown as dots in FIG. 3, is exchanged in $V_A$ 52 with carbon dioxide, shown as circles in FIG. 3. However, oxygen in the anatomical dead space volume 56 $VD_{ANA}$ is not exchanged with carbon dioxide. At the boundary between lungs 38 and airway 50, oxygen in $VD_{ANA}$ 56 commingles with carbon dioxide in $V_A$ 52, thereby creating a gradual transition between oxygen-rich gas in $VD_{ANA}$ 56 and carbon dioxide-rich gas in $V_A$ 56.

Figure 4A:
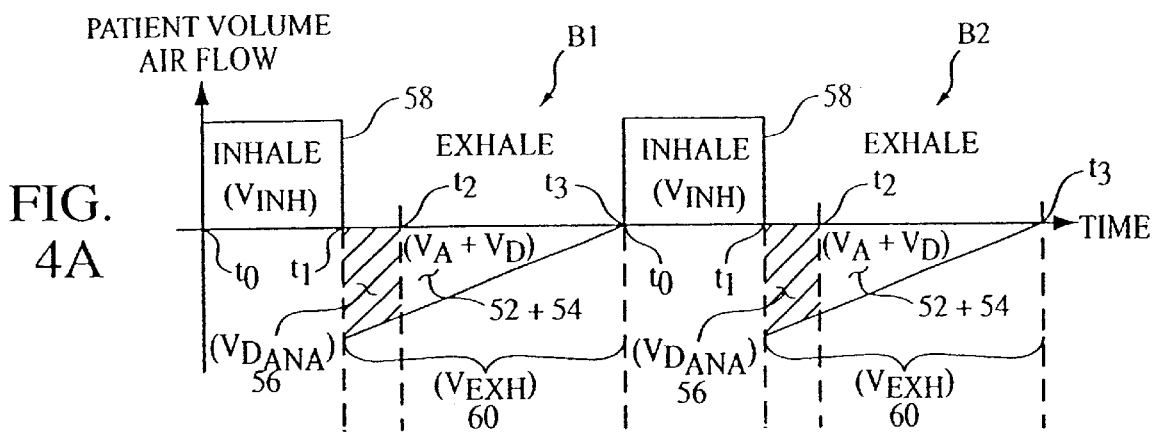
FIG. 4A is a time-based graph of the volumetric flow of gas over two breathing cycles of a patient.

With reference to FIG. 4A, and with ongoing reference to all previous figures, for each breath cycle of patient 8, controller 14 determines the volume of gas inhaled ($V_{INH}$) 58 between times $t_0$ and $t_1$ and the volume of gas exhaled ($V_{EXH}$) 60 between times $t_1$ and $t_3$ from the quantitative flow rate output from sensor 4. For each breath cycle, $V_{INH}$ 58 equals $V_{EXH}$ 60 which, equals the sum of $V_A$ 52, $V_D$ 54 and $VD_{ANA}$ 56.

Figure 4B:
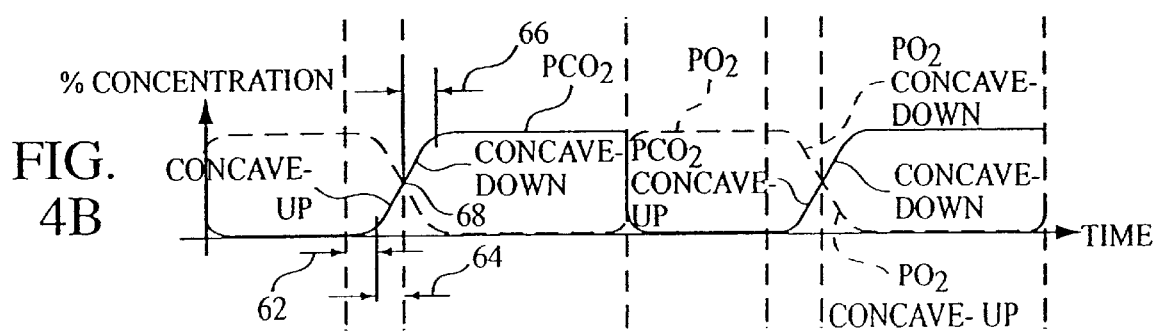
FIG. 4B is a time-based graph of percent concentration of carbon dioxide and oxygen for the two breathing cycles of FIG. 4A.

With reference to FIG. 4B, during inhalation between times $t_0$ and $t_1$, the percent concentration of carbon dioxide ($PCO_2$) is at or near zero percent and the percent concentration of oxygen ($PO_2$) is at or near the percent concentration of oxygen present in the breathing gas, such as air supplied to the patient. Because no exchange of carbon dioxide and oxygen occurs in airway 50, when patient 8 begins exhaling at time $t_1$, the oxygen-rich gas in $VD_{ANA}$ 56 is initially exhaled during an interval 62, which commences at time $t_1$. At the end of interval 62, patient 8 commences exhaling gas from the boundary of airway 50 and lungs 38. This gas includes oxygen in $VD_{ANA}$ 56 commingled with carbon dioxide in $V_A$ 52.

As shown in FIG. 4B, during an interval 64, which commences at the end of interval 62 and terminates at a time $t_2$, the $PCO_2$ in the exhaled gas gradually increases and the $PO_2$ in the exhaled gas gradually decreases due to the commingling of carbon dioxide-rich gas in $V_A$ 52 with the oxygen-rich gas in $VD_{ANA}$ 56. At time $t_2$, the rate of change of $PCO_2$ changes from increasing to decreasing due to the commingling of oxygen-rich gas from $VD_{ANA}$ 56 with carbon dioxide-rich gas in $V_A$ 52. Likewise, at time $t_2$, the rate of change of $PO_2$ changes from decreasing to increasing. Thereafter, during an interval 66, which commences at time $t_2$, the $PCO_2$ gradually increases to a maximum value at the end of interval 60, and the $PO_2$ gradually decreases to a minimum value at the end of interval 66. The maximum value of $PCO_2$ and the minimum value of $PO_2$ correspond to the gas being exhaled from a portion of $V_A$ 52, where no commingling between oxygen-rich gas in $VD_{ANA}$ 56 and carbon dioxide-rich gas in $V_A$ 52 occurs.

To detect $PCO_2$ or $PO_2$ in the gas exhaled by patient 8, controller 14 obtains multiple samples of the signal output by gas analyzer 6 between times $t_1$ and $t_3$ of a breath cycle. Controller 14 then evaluates the samples of the gas analyzer signal for an inflection point 68, where the rate of change of $PCO_2$ and/or $PO_2$ changes from increasing to decreasing, or vice versa. This change is graphically shown in FIG. 4B where a plot of $PCO_2$ is concave-up during interval 64 and concave-down during interval 66, and a plot of $PO_2$ is concave-down during interval 64 and concave-up during interval 66. Thus, by determining the inflection point 68, where the rate of change of $PCO_2$ and/or $PO_2$ changes from increasing to decreasing, or vice versa, controller 14 essentially determines for a plot of $PCO_2$ and/or a plot of $PO_2$ a change in direction of concavity from concave-up to concave-down, or vice versa.

To determine $VD_{ANA}$ 56, controller 14 determines time $t_1$ when patient 8 commences exhaling and time $t_2$ corresponding to the occurrence of inflection point 68, where the plot of $PCO_2$ and/or $PO_2$ changes direction of concavity. To determine time $t_1$, controller 14 determines when the signal produced by sensor 4 changes from a positive (+) sign during inhalation to a negative (−) sign during exhalation, or vice versa. Controller 14 interprets this change in sign as patient 8 commencing exhaling and records the time $t_1$ corresponding thereto.

Controller 14 also monitors the signal output by gas analyzer 6, determines inflection point 68 when the plot of the constituent concentration signal from the gas analyzer changes direction of concavity, and records the time $t_2$ when inflection point 68 occurs. Gas analyzer 6 preferably is a capnometer that detects $PCO_2$. However, gas analyzer 6 can also or alternatively detect $PO_2$.

Controller 14 integrates the volumetric flow signal produced by sensor 4 between times $t_1$ and $t_2$ and determines from this integration the volume of gas exhaled by patient 8 between times $t_1$ and $t_2$. This volume of exhaled gas corresponds to $VD_{ANA}$ 56, i.e., the patient's anatomical deadspace volume.

Figure 4C:
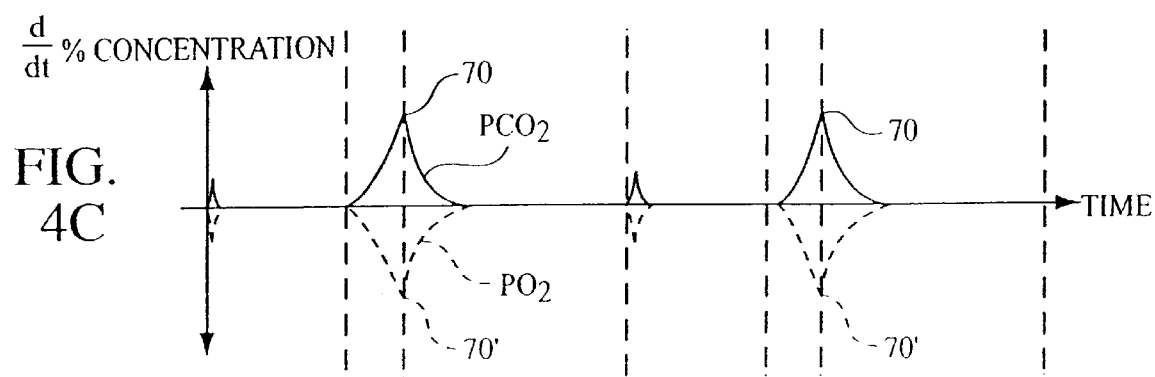
FIG. 4C is a graph of the first derivative of the percent concentration of carbon dioxide and oxygen for the two breathing cycles shown in FIG. 4B.

As discussed above, controller 14 can determine inflection point 68 and, hence time $t_2$, by determining when a plot of $PCO_2$ and $PO_2$ changes a direction of concavity. Alternatively, as shown in FIG. 4C, controller 14 calculates a first derivative of $PCO_2$ or $PO_2$ from the constituent concentration signal provided by the gas analyzer. Next, controller 14 determines when the peak value 70 or 70' of the first derivative of the constituent concentration signal for $PCO_2$ or $PO_2$, respectively, occurs after time $t_1$ and records time $t_2$ when peak value 70 or 70' occurs.

Figure 4D:
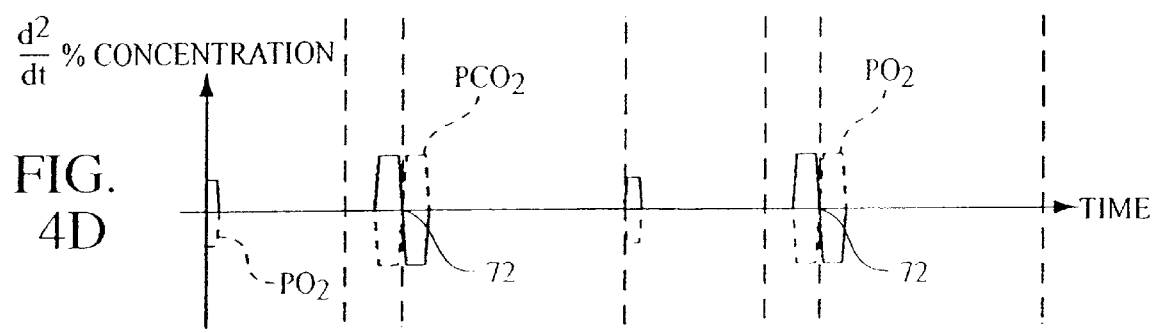
FIG. 4D is a graph of the second derivative of the percent concentration of carbon dioxide and oxygen for the two breathing cycles shown in FIG. 4B.

In another embodiment shown in FIG. 4D, controller 14 determines a second derivative of $PCO_2$ or $PO_2$ from the constituent concentration signal from the gas analyzer. Next, controller 14 determines an inflection point 72 when the second derivative has a value of zero and records time $t_2$ when inflection point 72 occurs. To ensure that inflection point 72 corresponds to inflection point 68, controller 14 determines a sign of the second derivative of the $PCO_2$ or $PO_2$ constituent concentration signal from the gas analyzer on opposite sides of inflection point 72 and determines if this second derivative changes signs on opposite sides of inflection point 72. More specifically, controller 14 determines if the sign (±) of the second derivative of the $PCO_2$ or $PO_2$ constituent concentration signal from the gas analyzer changes from positive to negative, or vice versa, at inflection point 72. If so, controller 14 interprets inflection point 72 as the time when the plot of $PCO_2$ or $PO_2$ in FIG. 4B changes concavity, i.e., as inflection point 68, and records time $t_2$ when the inflection point 72 occurs.

As discussed above, controller 14 determines from the signal produced by sensor 4, a time $t_1$ when patient 8 commences exhaling. Moreover, controller 14 can determine time $t_2$ by determining (i) when a plot of the $PCO_2$ or $PO_2$ constituent concentration signal produced by gas analyzer 6 changes direction of concavity; (ii) when peak value 70 or 70' of the first derivative of the $PCO_2$ or $PO_2$ constituent concentration signal from the gas analyzer occurs; or (iii) when the second derivative of the $PCO_2$ or $PO_2$ constituent concentration signal has a value of zero. Because the volume of gas exhaled by patient 8 between times $t_1$ and $t_2$ can be determined from the integral of the flow signal produced by sensor 4, controller 14 can determine for each breath cycle a value for the patient's anatomical deadspace volume $VD_{ANA}$ 56.

As can be seen, the present invention provides a method and apparatus for accurately and repeatedly determining an anatomical deadspace volume $VD_{ANA}$ of a patient. Based upon the thus determined patient anatomical deadspace volume, the operation of a ventilator, for example, can be controlled to fill the total lung volume of the patient with a breathing gas while avoiding patient discomfort and minimizing the medical risks to the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An apparatus for determining an anatomical deadspace volume $VD_{ANA}$ of a patient, the apparatus comprising:
   a sensor adapted to measure a parameter indicative of a volume of gas exhaled by a patient during at least an exhalation phase of a respiratory cycle;
   a gas analyzer adapted to measure a concentration of a gas constituent in such a patient's flow of gas during an exhalation phase of a respiratory cycle; and
   a controller operatively coupled to the sensor and the gas analyzer, wherein the controller determines such a patient's anatomical deadspace volume based on signals provided by the sensor and the gas analyzer.

2. The apparatus of claim 1, wherein the sensor is a flow sensor adapted to measure a rate of flow of gas exhaled by a patient over an exhalation phase of a respiratory cycle as the parameter indicative of a volume of gas exhaled by a patient, and wherein the controller uses the measured rate of flow of gas over the exhalation phase to determine the volume of gas exhaled by such a patient.

3. The apparatus of claim 1, wherein the gas analyzer is one of a capnometer and an oxygen analyzer.

4. The apparatus of claim 1, further comprising an output device operatively coupled to the controller and adapted to display information indicative of a patient's anatomical deadspace volume as determined by the controller.

5. The apparatus of claim 1, wherein the controller determines an anatomical deadspace volume of a patient by:
   determining a time $t_1$ that corresponds to a point at which such a patient commences exhaling;
   determining a time $t_2$ that corresponds to an inflection point in a waveform corresponding to the concentration of the gas constituent measured by the gas analyzer; and
   determines a volume of gas exhaled by such a patient from time $t_1$ to time $t_2$ as the anatomical deadspace volume of such a patient.

6. The apparatus of claim 5, wherein (1) if the gas analyzer is a capnometer, the inflection point is determined by the controller as corresponding to a point where the waveform changes from a concave-up shape to a concave-down shape, and (2) if the gas analyzer is an oxygen analyzer, the inflection point is determined by the controller as corresponding to a point where the waveform changes from a concave-down shape to a concave-up shape.

7. The apparatus of claim 5, wherein the controller determines time $t_2$ by determining a first derivative of the waveform and defines time $t_2$ as a point where a peak value of the first derivative of the waveform occurs.

8. The apparatus of claim 5, wherein the controller determines time $t_2$ by determining a second derivative of the waveform and defines time $t_2$ as a crossover point where the second derivative of the waveform has a value of zero.

9. The apparatus of claim 8, wherein the controller determines time $t_2$ by determining a sign (±) of the second derivative on opposite sides of the crossover point, and determining if the second derivative of the waveform changes sign on opposite sides of the crossover point.

10. The apparatus of claim 9, wherein the controller determines if the second derivative changes sign on opposite sides of the crossover point by also determining if the sign changes from one of positive to negative and negative to positive.

11. A method of determining an anatomical deadspace volume $VD_{ANA}$ of a patient, comprising:
    detecting a parameter indicative of a volume of gas exhaled by a patient;
    detecting a concentration of a gas constituent in a flow of gas exhaled by such a patient; and
    determining such a patient's anatomical deadspace volume based on the detected parameter indicative of a volume of gas and the detected concentration of a gas constituent.

12. The method of claim 11, the parameter indicative of a volume of gas exhaled is a rate of flow of gas exhaled by a patient over an exhalation phase of a respiratory cycle, and determining a patient's anatomical deadspace includes determining a volume of gas exhaled by such a patient based on the measured rate of flow of gas over the exhalation phase.

13. The method of claim 11, wherein detecting a concentration of a gas constituent includes (a) detecting a carbon dioxide as the gas constituent using a capnometer or (b) detecting oxygen as the gas constituent using an oxygen analyzer.

14. The method of claim 11, further comprising outputting information indicative of a patient's anatomical deadspace volume.

15. The method of claim 11, wherein determining such a patient's anatomical deadspace volume includes:
    determining a time $t_1$ that corresponds to a point at which such a patient commences exhaling;
    determining a time $t_2$ that corresponds to an inflection point in a waveform corresponding to the concentration of the gas constituent measured in the step of detecting a concentration of a gas constituent; and
    calculating a volume of gas exhaled by such a patient from time $t_1$ to time $t_2$ as the anatomical deadspace volume of such a patient.

16. The method of claim 15, wherein (1) if the step of detecting a concentration of a gas constituent is preformed using a capnometer, the inflection point is determined as corresponding to a point where the waveform changes from a concave-up shape to a concave-down shape, and (2) if the step of detecting a concentration of a gas constituent is preformed using a gas analyzer, the inflection point is determined as corresponding to a point where the waveform changes from a concave-down shape to a concave-up shape.

17. The method of claim 15, wherein determining time $t_2$ includes determining a first derivative of the waveform and defining time $t_2$ as a point where a peak value of the first derivative of the waveform occurs.

18. The method of claim 15, wherein determining time $t_2$ includes determining a second derivative of the waveform and defining time $t_2$ as a crossover point where the second derivative of the waveform has a value of zero.

19. The method of claim 18, wherein determining time $t_2$ includes determining a sign (±) of the second derivative on opposite sides of the crossover point and determining if the second derivative of the waveform changes sign on opposite sides of the crossover point.

20. The method of claim 19, wherein determining if the second derivative changes sign on opposite sides of the crossover point includes determining if the sign changes from one of positive to negative and negative to positive.

21. An apparatus for detecting an anatomical deadspace volume of a patient comprising:

sensing means for detecting a parameter indicative of a volume of gas exhaled by a patient;

gas analyzing means for detecting a concentration of a gas constituent in the flow of gas exhaled by such a patient; and processing means for determining such a patient's anatomical deadspace volume based on the detected volumetric flow of gas and the detected concentration of a gas constituent.

22. The apparatus of claim 21, further comprising outputting means for outputting information indicative of a patient's anatomical deadspace volume determined by the processing means.

23. The apparatus of claim 21, wherein the processing means determines the anatomical deadspace volume of a patient by:

determining a time $t_1$ that corresponds to a point at which such a patient commences exhaling;

determining a time $t_2$ that corresponds to an inflection point in a waveform corresponding to the concentration of the gas constituent measured by the gas analyzer; and calculating a volume of gas exhaled by such a patient from time $t_1$ to time $t_2$ as the anatomical deadspace volume of such a patient.

24. The apparatus of claim 23, wherein (1) if the gas analyzing means is a capnometer, the inflection point is determined by the processing means as corresponding to a point where the waveform changes from a concave-up shape to a concave-down shape, and (2) if the gas analyzing means is an oxygen analyzer, the inflection point is determined by the processing means as corresponding to a point where the waveform changes from a concave-down shape to a concave-up shape.

25. The apparatus of claim 23, wherein the processing means determines time $t_2$ by determining a first derivative of the waveform and defines time $t_2$ as a point where a peak value of the first derivative of the waveform occurs.

26. The apparatus of claim 23, wherein the processing means determines time $t_2$ by determining a second derivative of the waveform and defines time $t_2$ as a crossover point where the second derivative of the waveform has a value of zero.

27. The apparatus of claim 26, wherein the processing means determines time $t_2$ by determining a sign ($\pm$) of the second derivative on opposite sides of the crossover point, and determining if the second derivative of the waveform changes sign on opposite sides of the crossover point.

28. The apparatus of claim 27, wherein the processing means determines if the second derivative changes sign on opposite sides of the crossover point by also determining if the sign changes from one of positive to negative and negative to positive.

* * * * *